US012690997B2

(12) United States Patent
    Estrada

(10) Patent No.:    US 12,690,997 B2
(45) Date of Patent:         Jul. 28, 2026

(54) **INFANT LIMITED MOVEMENT
     RESTRAINER DEVICE**

(71) Applicant: Fidel Estrada, Hanover Park, IL (US)

(72) Inventor:  Fidel Estrada, Hanover Park, IL (US)

( * ) Notice:   Subject to any disclaimer, the term of this
                patent is extended or adjusted under 35
                U.S.C. 154(b) by 0 days.

(21) Appl. No.: 18/808,306

(22) Filed:     Aug. 19, 2024

(65)            Prior Publication Data

US 2025/0339304 A1     Nov. 6, 2025

Related U.S. Application Data

(60) Provisional application No. 63/642,986, filed on May
     6, 2024.

(51) Int. Cl.
     *A61F 5/37*          (2006.01)
(52) U.S. Cl.
     CPC .................................. *A61F 5/3784* (2013.01)
(58) Field of Classification Search
     CPC ...... A41B 13/06; A47D 15/008; A61F 5/3784
     USPC ..................... 5/482, 494, 603; 128/872, 869
     See application file for complete search history.

(56)            References Cited

U.S. PATENT DOCUMENTS 4,481,942  A      11/1984  Duncan
     4,653,131  A  *    3/1987  Diehl ..................... A47C 21/08
                                                         5/494

7,111,344  B2      9/2006  French
     8,375,486  B2      2/2013  Earnest
     8,695,133  B2  *   4/2014  Christensen ........... A41B 13/06
                                                         5/413 R
     2012/0311762 A1 *  12/2012  Aiken ..................... A41B 13/06
                                                         2/69.5
     2017/0258157 A1     9/2017  Pfanner
     2017/0325601 A1    11/2017  von Yurt
     2021/0259329 A1 *   8/2021  Kiik-Miley .......... A41B 13/005

FOREIGN PATENT DOCUMENTS

CN       213372845       6/2021
     CN       215131240      12/2021
     KR       101648237       8/2016

* cited by examiner

*Primary Examiner* — Justin C Mikowski
     *Assistant Examiner* — George Samuel Gines
     (74) *Attorney, Agent, or Firm* — KENECHTEL,
     DEMEUR & SAMLAN

(57)            ABSTRACT

A restraining device that limits the movement of an infant or
child while undergoing medical procedures and/or treat-
ment. In use, the restraining device is placed on a hospital or
treatment bed and secured to the bed using a plurality of
straps, the infant is then placed on top of the restraining
device with each arm of the infant being placed through a
hole in the restraining device, the respective holes reduced
in size to secure each arm within the hole of the restraining
device while simultaneously permitting or allowing each
arm to freely move, albeit with some limitation, under the
restraining device and the bed.

9 Claims, 4 Drawing Sheets

INFANT LIMITED MOVEMENT RESTRAINER DEVICE

I. CROSS-REFERENCE TO RELATED APPLICATION

This patent application is a non-provisional application claiming priority from U.S. Provisional Patent Application Ser. No. 63/642,986, entitled "Infant Limited Movement Restrainer Device", filed on May 6, 2024, and is fully incorporated herein by reference.

II. FIELD OF THE INVENTION

The present invention relates to a restrainer device for infants and, more particularly, to a restraining device that limits the movement of the infant or child while undergoing medical procedures and/or treatment.

III. BACKGROUND OF THE INVENTION

Restraining devices have been known in the art for a very long time, especially in the medical field. In all of that time, while there are, or have been, various restraining devices invented and/or in the prior art, each of these currently available devices and as further discussed below, were designed to solve a problem or are for use in connection with restraining infants, but each does so in a completely different manner. For example, U.S. Pat. No. 4,481,942 entitled "Infant Arm Restraint" discloses an arm restraint for application around the elbow of an infant to restrict movement of the infant's hands from certain areas. The arm restraint comprises a stiffening member formed into a generally cylindrical configuration about the arm of the infant.

U.S. Pat. No. 7,111,344 entitled "Infant Sleeping System" discloses a crib sheet with attachment points used to attach to the crib rails or bed frame. The crib sheet is used in combination with an infant sleep garment that attaches to the crib sheet by hook and loop mechanism. Attachment to the crib frame or bed frame, rather than the mattress, eliminates the risk that the infant's movements can cause the crib sheet to move or shift. Two points of attachment lie on either side of the shoulders or upper torso of the infant. The sleep garment has an arm restraint mechanism that acts to prevent movement of the infant's arms so that the infant cannot use its arms to escape the garment or to move itself about the crib or bed.

U.S. Pat. No. 8,375,486 entitled "Saddle Accessory" discloses a swaddle accessory to restrain an infant or child's arms has a single panel that is both wide and long enough to wrap entirely both of the infant's arms, hook and loop fasteners to secure the arm restraints and pockets to contain the hands to prevent them from breaking out of a swaddle made from a receiving blanket or other swaddle device.

Korean Patent KR 101648237B1 entitled "Swaddle Blanket" discloses batting blankets and a mattress attachment apparatus. The wrapper blanket includes an upper end and a lower end, and a pocket disposed at the lower end and is configured to surround the leg of the infant. The mattress attachment device is configured to be secured to the outer skin for sleeping.

In all of this time, while the restraining devices disclosed in the above-identified patents and maybe currently available, and/or also for use with infants, the current issue remains unresolved as they provide restraining of an infant in different ways solving different problems; but, none of them disclose being able to restrain an infant while the infant is undergoing medical procedures and/or treatment while also permitting or allowing limited movement (although freely within this area) of the infant and its arms without affecting or causing any issues with the medical procedures and/or treatment.

Applicant, on the other hand, has solved this problem. Thus, there is a need, therefore, and there has never been disclosed Applicant's unique infant limited movement restrainer device and method of using the same.

IV. SUMMARY OF THE INVENTION

The present invention is a restraining device that limits the movement of an infant or child while undergoing medical procedures and/or treatment. In use, the restraining device is placed on a hospital or treatment bed and secured to the bed using a plurality of straps, the infant is then placed on top of the restraining device with each arm of the infant being placed through a hole in the restraining device, the respective holes reduced in size to secure each arm within the hole of the restraining device while simultaneously permitting or allowing each arm to freely move, albeit with some limitation, under the restraining device and the bed.

V. BRIEF DESCRIPTION OF THE DRAWINGS

The Description of the Preferred Embodiment will be better understood with reference to the following figures.

VI. DETAILED DESCRIPTION OF THE PREFERRED EMBODIMENT

Figure 1:
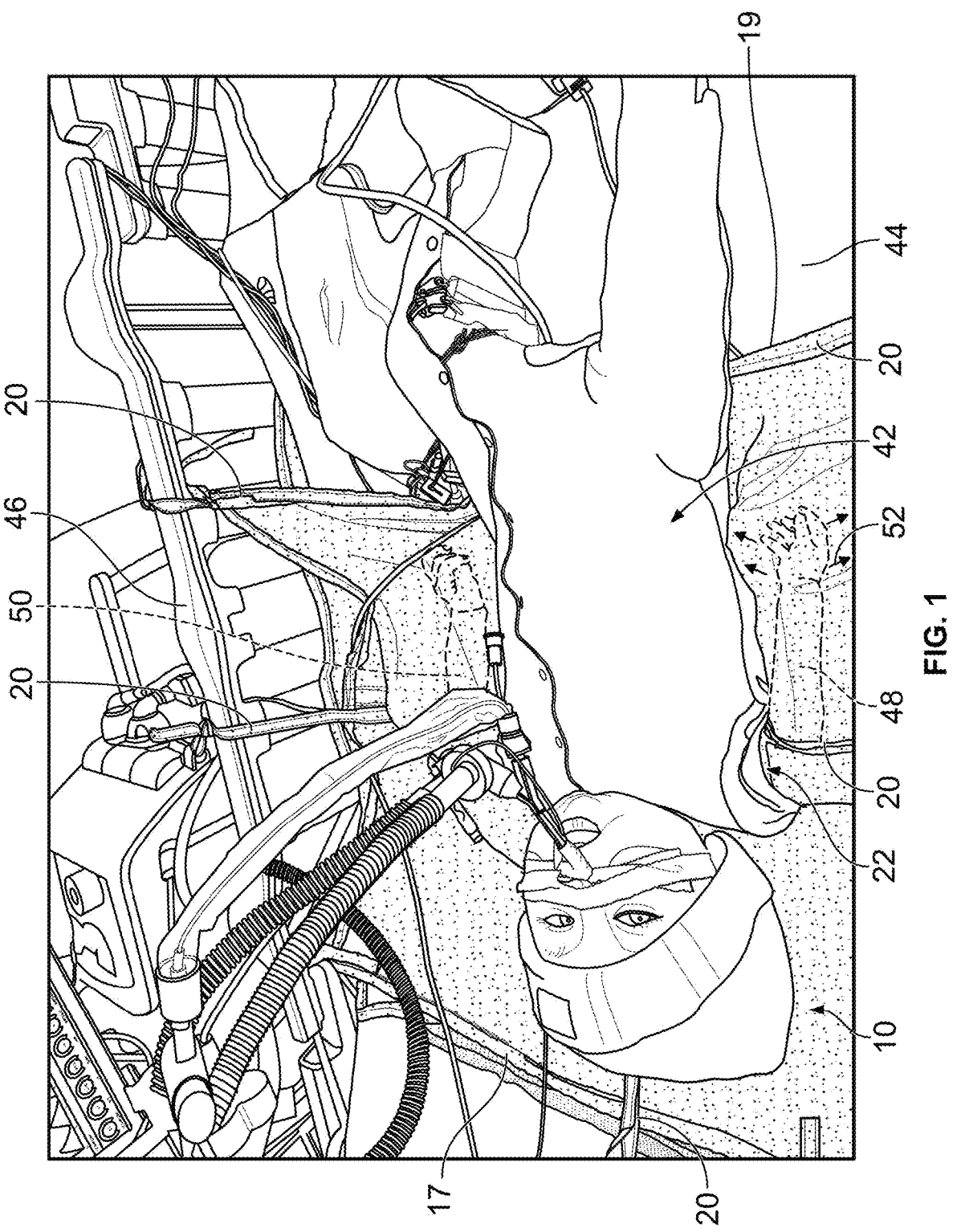
FIG. 1 is a perspective view of Applicant's inventive infant limited movement restrainer device and manufactured in accordance with the present invention and, in particular, illustrating the components and assembly of the infant limited movement restrainer device in accordance with the present invention and as shown in a type of use with an infant or child patient.

While this invention is susceptible of embodiment in many different forms, there is shown in the drawings and described herein in detail specific embodiments with the understanding that the present disclosure is to be considered as an exemplification of the principles of the invention and is not intended to limit the invention to the embodiments illustrated.

It will be understood that like or analogous elements and/or components, referred to herein, may be identified throughout the drawings with like reference characters. It will be further understood that FIGS. 1-4 are merely schematic representations of the device and some of the components may have been distorted from their actual scale for pictorial clarity.

In accordance with the present invention, and referring to FIG. 1, Applicant's infant limited movement restrainer device 10 is designed to restrain an infant or child patient 42 during medical procedures and/or treatment, as illustrated and/or which may include, without limitation, applications such as IV/LL/Peripheral IA, UAC/UVC insertion, lumbar puncture, intubation, chest drain insertion, transports, etc., or any other possible application in which Applicant's device may be applicable or used.

Figure 2:
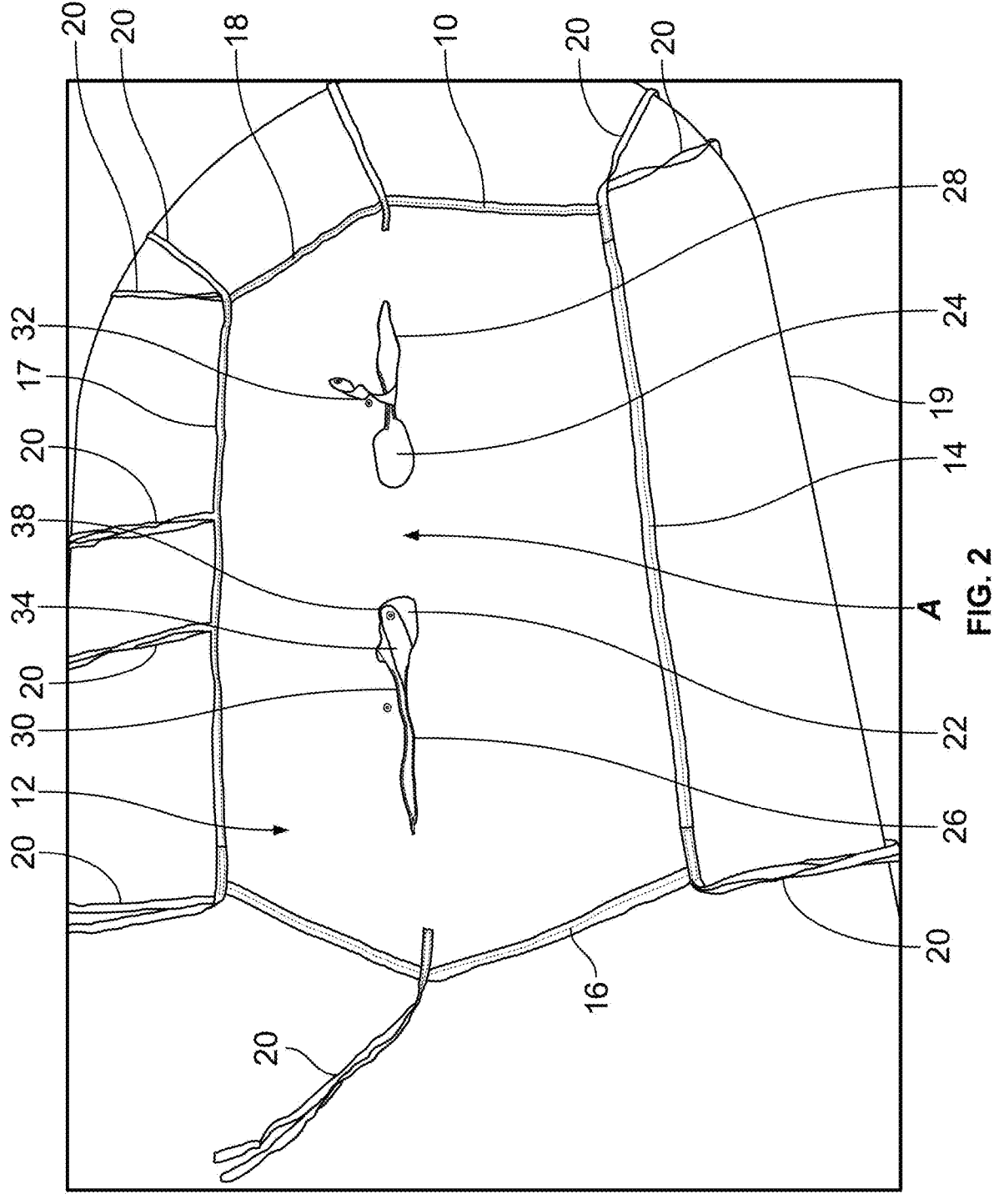
FIG. 2 is a top view of Applicant's inventive infant limited movement restrainer device and manufactured in accordance with the present invention and, in particular, illustrating the components and assembly of the infant limited movement restrainer device in accordance with the present invention.
Figure 3:
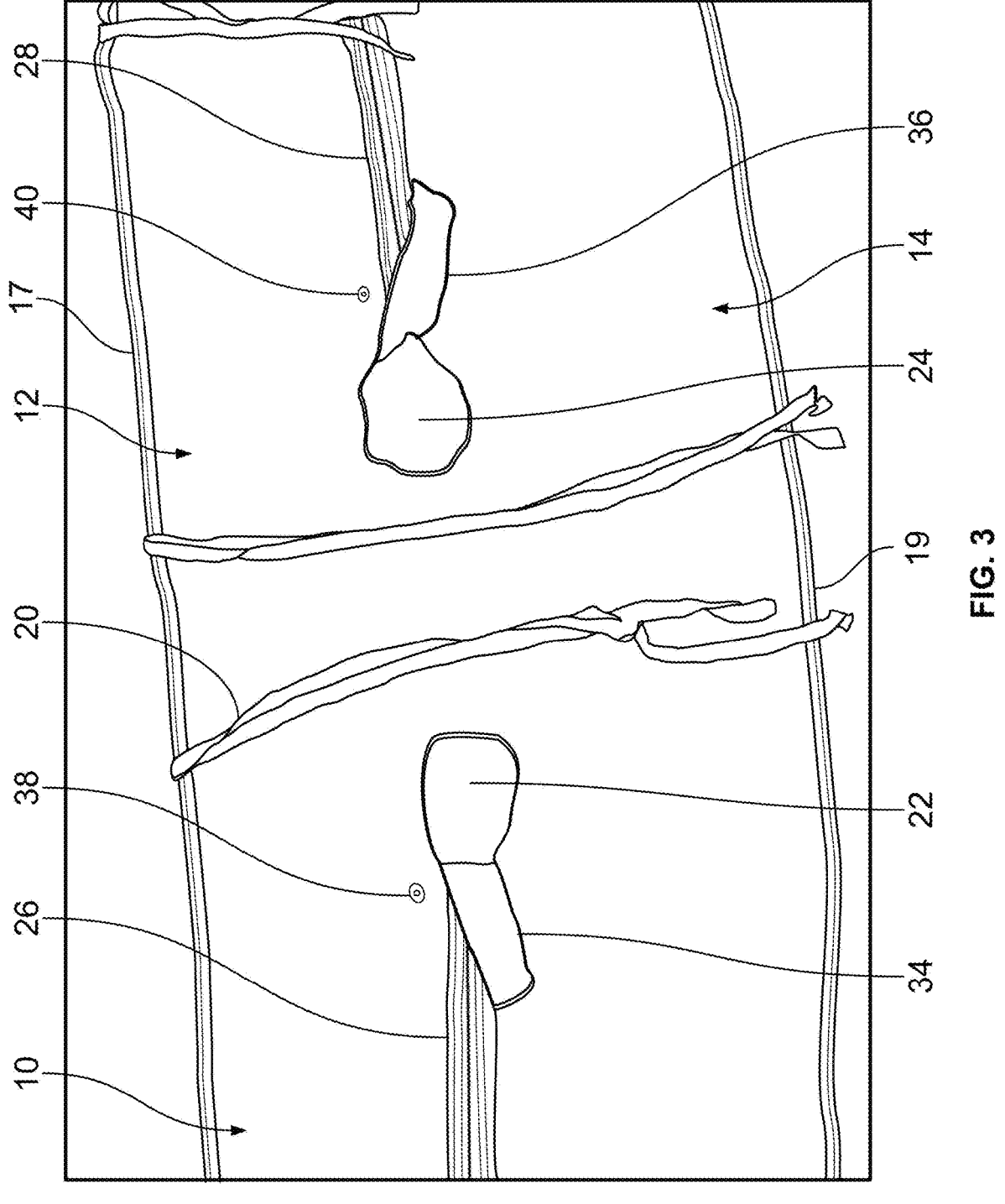
FIG. 3 is a back view of Applicant's inventive infant limited movement restrainer device and manufactured in accordance with the present invention and, in particular, illustrating the components and assembly of the infant limited movement restrainer device in accordance with the present invention.
Figure 4:
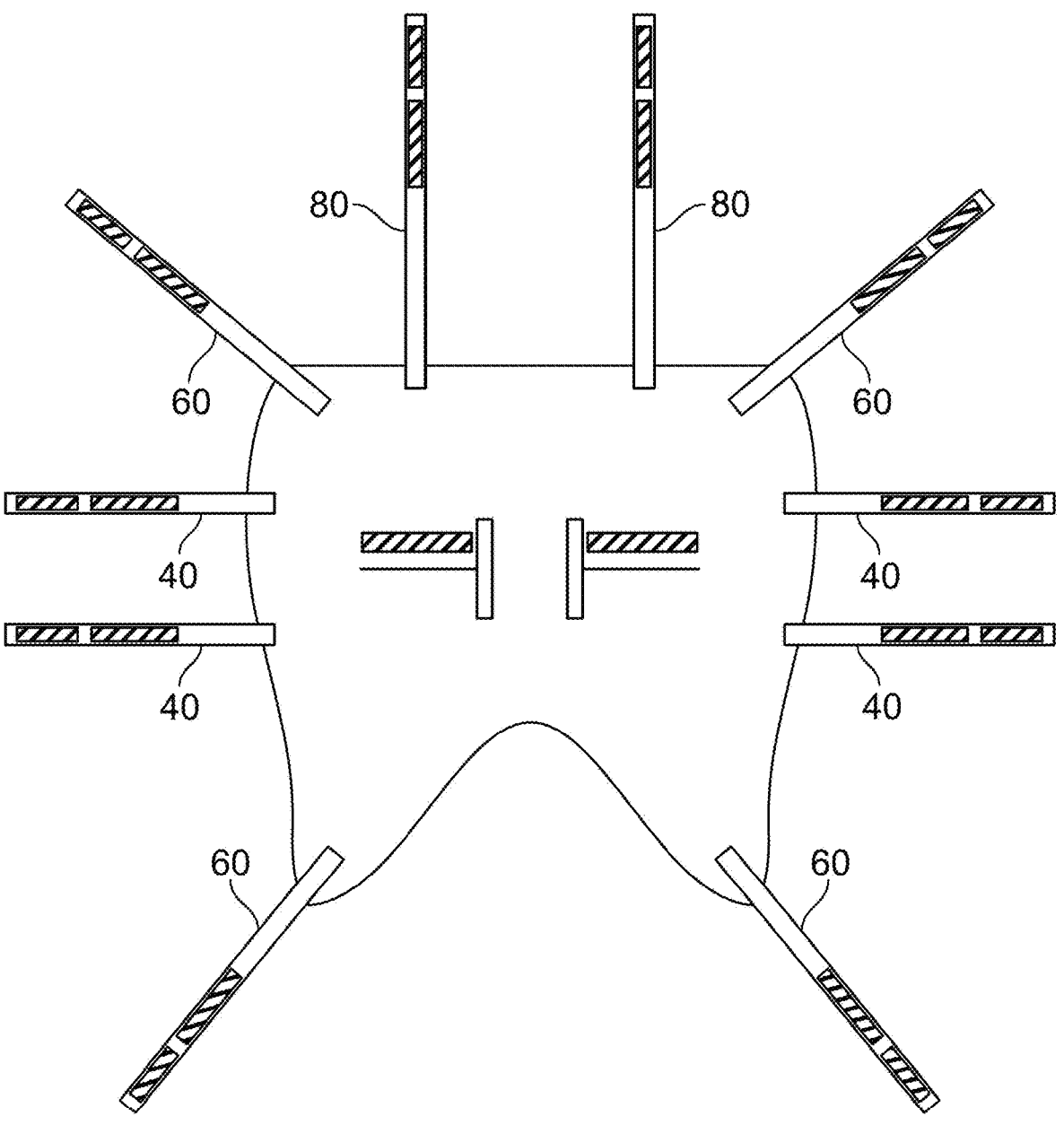
FIG. 4 is a top view (illustration) of Applicant's inventive infant limited movement restrainer device and manufactured in accordance with the present invention and, in particular, illustrating various dimension of the components and assembly of the infant limited movement restrainer device in accordance with the present invention.

Referring to FIGS. 2 and 3, the infant limited movement restrainer device 10 is an elongated, thin device that has a top surface 12, a bottom surface 14, and left side 16 and right side 18, and top side 17 and bottom side 19, In the preferred embodiment, the device 10 is placed on a bed 44 (e.g., frame or any other type of support) under the infant or child patient 42 (as shown in FIG. 1), and using the straps 20, with each of the top surface 12, bottom surface 12, left side 16, and right side 18 connected to an adjacent bar or handle 46 or other part of the bed 44 (as shown in FIG. 1), thereby, securing the device 10 to the bed 44. Alternatively, the straps 20, may extend from the top side 17 and/or bottom side 19 and be connected to an adjacent bar or handle 46 or other part of the bed 44 as well, thereby, securing the device 10 to the bed 44 in this manner. Preferably, the straps 20 have the dimensions 60 and 80 as shown in FIG. 4, with the straps 20 having the dimensions 60 being slightly smaller than the straps 20 having the dimensions 80, although any dimensions 60 and 80 known to one skilled in the art may work provided the device 10 is used as described herein.

Located within the device 10 are holes 22, 24, each situated adjacent to a zipper 26, 28. The infant or child patient 42 is placed on their back on top of the device 10 between the holes 22, 24, at location A, with one arm 48 (as shown in FIG. 1) of the infant or child patient 42 situated adjacent to hole 22 and the other arm 50 (as shown in FIG. 1) situated adjacent to hole 24. The zipper 26, 28 for each hole 22, 24 are opened to create a further enlarged hole 30, 32. The infant or child patient 42 arm 48 is placed through the enlarged hole 30 and the other of the infant or child patient 42 arm 50 is placed through the enlarged hold 32. In this manner, while the infant or child patient 42 body is above or on top of the device 10, each of the infant or child patient 42 arms 48, 50 are now located under the device 10 (as shown in FIG. 1). Each of the zipper 26, 28 are then closed such that the enlarged hold 30, 32 are closed leaving the infant or child patient 42 arms 48, 50 situated only within and through the holes 22, 24. Flaps 34, 36, and buttons 38, 40 are used to cover the zipper 26, 28 to prevent any chaffing or other discomfort from the zipper 26, 28 to the infant or child patient 42 arms 48, 50. In the preferred embodiment, the holes 22, 24 have a diameter that is large enough to accommodate the infant or child patient 42 arms 48, 50 with a sufficient clearance not to constrict the arms 48, 50 at all, but also not enough clearance to allow the infant or child patient 42 to pull their arms 48, 50 back through, or remove from, the holes 22, 24.

In an alternate embodiment, it is contemplated that other than arms 48, 50, any appendage of the patient 42 may be used and secured by the holes 22, 24. And, it is further contemplated that the secured appendages may likewise be moveable within (or inside) the elongated member between the top surface and the bottom surface.

At this point, while the infant or child patient 42 arms 48, 50 are situated and limited within the holes 22, 24, the infant or child patient 42 is free to move their arms 48, 50 anywhere under the device 10 and within the open space or clearance 52 (as shown in FIG. 1).

Additionally, the left side 16 and right side 18 of the device 10 are tapered outwardly to the applicable strap 20, thus, providing additional coverage of the device 10 which, in turn, provides additional open space or clearance 52 under the device 10 for the infant or child patient 42 to move their arms 48, 50 (e.g., including limited movement upwards as the device 10 with this tapering will allow such additional movement.

Based on the foregoing, Applicant's device 10 provides at least the following advantages:

(a) Providing a means to restrain an infant to restrain any limbs, and particularly their arms, while on the bed for a medical procedure or treatment;

(b) Allowing the infant's limbs, and particularly their arms, limited movement (although freely within this area) including along the infant's side, down, up, and around—all permitted under the device 10;

(c) While the movement is limited, the infant still feels like they have their typical movement that they are used to and this then is one less burdensome or discomfort to the infant hopefully allowing the medical procedure or treatment to proceed less abated by the infant;

Thus, there has been provided a infant limited movement restrainer device and method of using the same. While the invention has been described in conjunction with a specific embodiment, it is evident that many alternatives, modifications and variations will be apparent to those skilled in the art in light of the foregoing description. Accordingly, it is intended to embrace all such alternatives, modifications and variations as fall within the spirit and scope of the disclosure contained herein and appended claims.

What is claimed is:

1. A device for use with an infant, comprising:

an elongated member having a top surface and a bottom surface and forming a single layer; the top surface and the bottom surface forming opposed sides of the elongated member;

a first hole situated through the elongated member and the top surface and the bottom surface;

a second hole situated through the elongated member and the top surface and the bottom surface;

the first hole and the second hole located adjacent to one another and creating a space between them on top of the top surface;

a first elongated hole in communication with first hole and extending outwardly from the first hole in a direction away from the space, the first hole and the first elongated hole co-acting to create a combined first larger hole;

a first zipper to per and close the first elongated hole;

a second elongated hole in communication with the second hole and extending outwardly from the second hole in a direction away from the space, the second hole and the second elongated hole co-acting to create a combined second larger hole;

a second zipper to open and close the second elongated am hole;

a plurality of straps extending outwardly from the elongated member;

wherein, when in use, the elongated member is placed on a bed and secured to the bed using the plurality of straps, the infant is then placed in the space on top of the top surface of the elongated member, an arm of the infant is placed through the combined first larger hole with the first zipper being used to reduce the size of the combined first larger hole to secure the arm within the first hole, another arm of the infant is placed through the combined second larger hole with the second zipper being used to reduce the size of the combined second larger hole to secure the another arm within the second hole, the arm and the another arm freely moveable under the bottom surface of the elongated member and the bed, the arm and the another arm having full range of motion under the bottom surface of the elongated member.

2. The device of claim 1 wherein the first hole and the second hole are substantially identical.

3. The device of claim 1 wherein the elongated member further comprises a left side, and a right side.

4. The device of claim 3 wherein the left side of the elongated member tapers outwardly from the top surface to a center of the left side.

5. The device of claim 4 wherein the left side of the elongated member tapers outwardly from the bottom surface to the center of the left side.

6. The device of claim 3 wherein the right side of the elongated member tapers outwardly from the top surface to a center of the right side.

7. The device of claim 6 wherein the right side of the elongated member tapers outwardly from the bottom surface to the center of the right side.

8. The device of claim 1 and further comprising a first flap to cover the first zipper at an intersection of the first elongated hole and the first hole.

9. The device of claim 1 and further comprising a second flap to cover the second zipper at an intersection of the second elongated hole and the second hole.

* * * * *